(12) United States Patent
Alon

(10) Patent No.: US 10,299,928 B2
(45) Date of Patent: May 28, 2019

(54) HEART VENTRICLE REMODELING

(71) Applicant: David Alon, Zichron Yaacov (IL)

(72) Inventor: David Alon, Zichron Yaacov (IL)

( * ) Notice: Subject to any disclaimer, the term of this patent is extended or adjusted under 35 U.S.C. 154(b) by 92 days.

(21) Appl. No.: 15/540,974

(22) PCT Filed: Dec. 23, 2015

(86) PCT No.: PCT/IB2015/002415
§ 371 (c)(1),
(2) Date: Jun. 29, 2017

(87) PCT Pub. No.: WO2016/110735
PCT Pub. Date: Jul. 14, 2016

(65) Prior Publication Data
US 2018/0000589 A1    Jan. 4, 2018

Related U.S. Application Data

(60) Provisional application No. 62/099,973, filed on Jan. 5, 2015.

(51) Int. Cl.
*A61F 2/24* (2006.01)
*A61B 17/00* (2006.01)
*A61N 1/05* (2006.01)

(52) U.S. Cl.
CPC .......... *A61F 2/2478* (2013.01); *A61F 2/2487* (2013.01); *A61B 2017/00243* (2013.01); *A61F 2002/2484* (2013.01); *A61N 1/057* (2013.01)

(58) Field of Classification Search
CPC ................. A61F 2/2478; A61F 2/2487; A61F 2002/2484; A61N 1/057; A61B 2017/00243

USPC ..................................... 600/37; 128/897–898
See application file for complete search history.

(56) References Cited

U.S. PATENT DOCUMENTS

| | | | |
|---|---|---|---|
| 2006/0287661 A1* | 12/2006 | Bolduc ............ | A61B 17/00234 606/153 |
| 2007/0066863 A1 | 3/2007 | Rafiee et al. | |
| 2007/0112338 A1* | 5/2007 | Cohen ................ | A61B 17/0401 606/1 |

(Continued)

FOREIGN PATENT DOCUMENTS

WO    2011034973 A2    3/2011

OTHER PUBLICATIONS

International Search Report and Written Opinion for International Application No. PCT/IB2015/002415 dated Apr. 1, 2016.

(Continued)

*Primary Examiner* — Navin Natnithithadha
*Assistant Examiner* — Sunita Reddy
(74) *Attorney, Agent, or Firm* — Potomac Law Group, PLLC

(57) ABSTRACT

The ventricle of a heart can be reshaped by passing a plurality of catheters from inside the ventricle to outside the ventricle through holes in the ventricle wall. Fluid-tight bags are then delivered through the catheters and expanded outside the ventricle to a diameter that is larger than the holes. A fluid substance is introduced into the bags, and the fluid substance is configured to solidify into solid pads that are also larger than the holes. The solid pads are then pulled towards each other and locked in position in order to reshape the ventricle.

19 Claims, 14 Drawing Sheets

(56) References Cited

U.S. PATENT DOCUMENTS

| | | | |
|---|---|---|---|
| 2007/0198038 A1* | 8/2007 | Cohen | A61B 17/0401 606/150 |
| 2007/0203391 A1* | 8/2007 | Bloom | A61B 17/00234 600/37 |
| 2008/0027268 A1* | 1/2008 | Buckner | A61B 17/00234 600/16 |
| 2008/0082132 A1 | 4/2008 | Annest et al. | |
| 2008/0269551 A1* | 10/2008 | Annest | A61B 17/00234 600/37 |
| 2008/0294251 A1* | 11/2008 | Annest | A61B 17/0401 623/3.1 |
| 2010/0004504 A1* | 1/2010 | Callas | A61F 2/2478 600/37 |
| 2010/0022821 A1* | 1/2010 | Dubi | A61B 17/00234 600/37 |
| 2011/0060407 A1* | 3/2011 | Ketai | A61B 17/00234 623/2.37 |
| 2011/0092988 A1* | 4/2011 | Cohen | A61B 17/0057 606/142 |
| 2011/0190879 A1* | 8/2011 | Bobo | A61F 2/2445 623/2.37 |
| 2015/0342737 A1* | 12/2015 | Biancucci | A61F 2/2442 600/37 |

OTHER PUBLICATIONS

Pedersen et al., "The iCoapsys Repair System for the percutaneous treatment of functional mitral insufficiency", EuroIntervention, May 20, 2006, 1(Supplement A), pp. A44-A48.

* cited by examiner

HEART VENTRICLE REMODELING

CROSS REFERENCE TO RELATED APPLICATIONS

This Application is a U.S. national stage filing under 35 U.S.C. § 371 of International Application No. PCT/IB2015/002415 filed Dec. 23, 2015, which claims the benefit of U.S. Provisional Application No. 62/099,973,filed Jan. 5, 2015, each of which is incorporated herein by reference in its entirety.

BACKGROUND

The present invention relates to a device for repairing a dilated heart ventricle by reshaping it mechanically.

Heart failure (HF), often called congestive heart failure (CHF) or congestive cardiac failure (CCF), occurs when the heart is unable to provide sufficient pump action to distribute blood flow to meet the needs of the body. Heart failure can cause a number of symptoms including shortness of breath, leg swelling, exercise intolerance, and even death.

Common causes of heart failure include myocardial infarction and other forms of ischemic heart disease, hypertension, valvular heart disease, and cardiomyopathy.

Cardiomyopathy (literally "heart muscle disease") is the measurable deterioration of the function of the myocardium (the heart muscle) for any reason, usually leading to heart failure. Common symptoms are dyspnea (breathlessness) and peripheral edema (swelling of the legs). People with cardiomyopathy are often at risk of dangerous forms of irregular heart beat and sudden cardiac death. The most common form of cardiomyopathy is dilated cardiomyopathy.

Dilated cardiomyopathy (DCM) is a condition in which the heart becomes weakened and enlarged and cannot pump blood efficiently. In DCM a portion of the myocardium is dilated, often without any obvious cause. Left or right ventricular systolic pump function of the heart is impaired, leading to progressive cardiac enlargement and hypertrophy, a process called remodeling.

Dilated cardiomyopathy is the most common form of non-ischemic cardiomyopathy. It occurs more frequently in men than in women, and is most common between the ages of 20 and 60 years. About one in three cases of congestive heart failure (CHF) is due to dilated cardiomyopathy. Dilated cardiomyopathy also occurs in children.

Another common symptom of heart dilatation is the onset of Mitral valve insufficiency commonly called functional MR. Functional MR results from loss of coaptation of the valve leaflets characterized by dilatation of the mitral valve annulus or papillary muscle displacement with chordae tethering, and is as well considered as an ongoing impetus of progression for dilated cardiomyopathy.

To date, there is no surgical or other interventional treatment for the shape deterioration or remodeling of the heart. Current treatment methods depend on the type of cardiomyopathy and condition of the disease, and may include medication (a conservative treatment) or interventions intended for management of heart arrhythmias. Such treatment methods may include implanted pacemakers for slow heart rates, defibrillators for those prone to fatal heart rhythms, or ablations for recurring arrhythmias that cannot be eliminated by medication or pacemakers. The goal of treatment is often symptom relief, but not the actual cure of the disease. In severe heart failure cases patients may require ventricular assist devices and eventually a heart transplant.

Not many attempts were made to develop surgical or interventional devices for mechanical re-shaping of the dilated heart. One of the most notable attempts was made by the Coapsys device which was designed to reverse the remodeling of the left ventricle and treat functional MR.

The Coapsys device consisted of posterior and anterior extracardiac pads implanted surgically and connected by a flexible, transventricular subvalvular cord. By shortening that cord after the pads were in place, the ventricular walls were drawn together and the mitral annulus and subvalvular apparatus were compressed. The re-shaping of the Mitral annulus improved coaptation of the valve leaflets and reduced the MR grade. The device also decreased direct left ventricular wall stress and induced positive ventricular remodeling. Unfortunately, the implantation of the Coapsys device is implemented through a median sternotomy on a beating heart.

SUMMARY OF THE INVENTION

The present invention relates to method and apparatus for percutaneous reshaping of a heart ventricle, typically the left ventricle. The apparatus is consists of two or more pads made out of a fluid that has solidified (typically thermosetting polymer) placed outside of the heart, and pulled together from within the heart to reshape the ventricle. The procedure is preferably done percutaneously, off pump, on a beating heart either through a puncture in the left atrium or through a catheter advanced through the vascular system.

One aspect of the invention is directed to an apparatus for reshaping a ventricle of a heart. The ventricle has a first wall section and a second wall section that is disposed opposite to the first wall section. This apparatus includes a first fluid-tight bag having a first inlet that is configured to accept a fluid and a distal end that is configured to pass through a first hole in the first wall section and extend outside the ventricle, and the first fluid-tight bag is configured so that when the distal end has passed through the first hole and has been extended outside the ventricle, at least a portion of the distal end that extends outside the ventricle has a diameter that is larger than the first hole. This apparatus also includes a first solid filler material disposed outside the ventricle in the distal end of the first fluid tight bag. The first solid filler material has a diameter that is larger than the first hole, and the first solid filler material is formed by introducing at least one fluid substance into the first fluid tight bag via the first inlet after the distal end of the first fluid tight bag has passed through the first hole and has been extended outside the ventricle. The at least one fluid substance is configured to solidify after being introduced into the first fluid tight bag. This apparatus also includes a second fluid-tight bag that has a second inlet that is configured to accept a fluid and a distal end that is configured to pass through a second hole in the second wall section and extend outside the ventricle. The second fluid-tight bag is configured so that when the distal end has passed through the second hole and has been extended outside the ventricle, at least a portion of the distal end that extends outside the ventricle has a diameter that is larger than the second hole. This apparatus also includes a second solid filler material disposed outside the ventricle in the distal end of the second fluid tight bag. The second solid filler material has a diameter that is larger than the second hole, and the second solid filler material is formed by introducing at least one fluid substance into the second fluid tight bag via the second inlet after the distal end of the second fluid tight bag has passed through the second hole and has been extended outside the ventricle. The at least one fluid substance is configured to solidify after being introduced into the second fluid tight bag. This apparatus also includes an elongated member that has a first end and a second end. The first end of the elongated member is attached to the first solid filler material and the second end of the elongated member is attached to the second solid filler material, and the elongated member is configured to pull the first solid filler material towards the second solid filler material.

In some embodiments, the first fluid-tight bag has a first tube-shaped proximal portion that is connected to the distal end of the first fluid-tight bag, and the second fluid-tight bag has a second tube-shaped proximal portion that is connected to the distal end of the second fluid-tight bag. In some embodiments, the elongated member is formed by attaching the first tube-shaped proximal portion to the second tube-shaped proximal portion. In some embodiments, the elongated member includes a first section of tubing that is attached to the first solid filler material and a second section of tubing that is attached to the second solid filler material, and the first section of tubing is attached to the second section of tubing. In some embodiments, the elongated member includes a first section of catheter that is attached to the first solid filler material and a second section of catheter that is attached to the second solid filler material, and the first section of catheter is attached to the second section of catheter. In some embodiments, the first solid filler material has a diameter of at least 2 cm and the second solid filler material has a diameter of at least 2 cm. In some embodiments, the first solid filler material has a diameter between 3 and 6 cm and the second solid filler material has a diameter between 3 and 6 cm.

Another aspect of the invention is directed to an apparatus for reshaping a ventricle of a heart. The ventricle has a first wall section and a second wall section that is disposed opposite to the first wall section. This apparatus includes a first catheter configured to pass from inside the ventricle to outside the ventricle through a first hole in the first wall section. The first catheter has a first lumen. This apparatus also includes a first fluid-tight bag having a first inlet that is configured to accept a fluid and a distal end that is configured to pass through the first lumen and through the first hole in the first wall section and extend outside the ventricle. The first fluid-tight bag is configured so that when the distal end has passed through the first hole and has been extended outside the ventricle, at least a portion of the distal end that extends outside the ventricle has a diameter that is larger than the first hole. This apparatus also includes a first substance configured for introduction into the first fluid tight bag in a fluid state via the first inlet after the distal end of the first fluid tight bag has passed through the first hole and has been extended outside the ventricle. The first substance is configured to solidify after being introduced into the first fluid tight bag. This apparatus also includes a second catheter configured to pass from inside the ventricle to outside the ventricle through a second hole in the second wall section. The second catheter has a second lumen. This apparatus also includes a second fluid-tight bag having a second inlet that is configured to accept a fluid and a distal end that is configured to pass through the second lumen and through the second hole in the second wall section and extend outside the ventricle. The second fluid-tight bag is configured so that when the distal end has passed through the second hole and has been extended outside the ventricle, at least a portion of the distal end that extends outside the ventricle has a diameter that is larger than the second hole. This apparatus also includes a second substance configured for introduction into the second fluid tight bag in a fluid state via the second inlet after the distal end of the second fluid tight bag has passed through the second hole and has been extended outside the ventricle, and the second substance is configured to solidify after being introduced into the second fluid tight bag. This apparatus also includes an elongated member adapted to pull the first substance towards the second substance after the first substance and the second substance have solidified.

In some embodiments, the first fluid-tight bag has a first tube-shaped proximal portion that is connected to the distal end of the first fluid-tight bag, and the second fluid-tight bag has a second tube-shaped proximal portion that is connected to the distal end of the second fluid-tight bag. In some embodiments, the elongated member is formed by attaching the first tube-shaped proximal portion to the second tube-shaped proximal portion. In some embodiments, the apparatus further includes a first plunger configured to push the first substance through the first tube-shaped proximal portion into the distal end of the first fluid tight bag while the first substance is in a fluid state, and a second plunger configured to push the second substance through the second tube-shaped proximal portion into the distal end of the second fluid tight bag while the second substance is in a fluid state. In some embodiments, the first plunger is further configured to facilitate withdrawal of the first plunger via the first tube-shaped proximal portion after the first substance has solidified, and the second plunger is further configured to facilitate withdrawal of the second plunger via the second tube-shaped proximal portion after the second substance has solidified.

In some embodiments, the elongated member includes (a) a section of the first catheter and (b) a section of the second catheter that is connected to the section of the first catheter. In some embodiments, the first fluid-tight bag is configured so that when the distal end has passed through the first hole and has been extended outside the ventricle, at least a portion of the distal end that extends outside the ventricle has a diameter of at least 2 cm, and the second fluid-tight bag is configured so that when the distal end has passed through the second hole and has been extended outside the ventricle, at least a portion of the distal end that extends outside the ventricle has a diameter of at least 2 cm. In some embodiments, the first fluid-tight bag is configured so that when the distal end has passed through the first hole and has been extended outside the ventricle, at least a portion of the distal end that extends outside the ventricle has a diameter between 3 and 6 cm, and the second fluid-tight bag is configured so that when the distal end has passed through the second hole and has been extended outside the ventricle, at least a portion of the distal end that extends outside the ventricle has a diameter between 3 and 6 cm.

Another aspect of the invention is directed to a method for reshaping a ventricle of a heart. The ventricle has a first wall section and a second wall section that is disposed opposite to the first wall section. This method includes the steps of: (a) passing a first catheter having a first lumen from inside the ventricle to outside the ventricle through a first hole in the first wall section; (b) delivering, through the first catheter, a first fluid-tight bag having a first inlet that is configured to accept a fluid and a distal end that is configured to pass through the first lumen and through the first hole in the first wall section; (c) extending the distal end of the first fluid-tight bag outside the ventricle so that at least a portion of the distal end of the first fluid-tight bag has a diameter that is larger than the first hole; (d) introducing a first substance into the first fluid tight bag in a fluid state via the first inlet after the distal end of the first fluid tight bag has been extended, wherein the first substance is configured to solidify after being introduced into the first fluid tight bag; (e) passing a second catheter having a second lumen from inside the ventricle to outside the ventricle through a second hole in the second wall section; (f) delivering, through the second catheter, a second fluid-tight bag having a second inlet that is configured to accept a fluid and a distal end that is configured to pass through the second lumen and through the second hole in the second wall section; (g) extending the distal end of the second fluid-tight bag outside the ventricle so that at least a portion of the distal end of the second fluid-tight bag has a diameter that is larger than the second hole; (h) introducing a second substance into the second fluid tight bag in a fluid state via the second inlet after the distal end of the second fluid tight bag has been extended, wherein the second substance is configured to solidify after being introduced into the second fluid tight bag; and (i) pulling the first substance towards the second substance after the first substance and the second substance have solidified.

In some embodiments, the step of introducing the first substance is implemented by pushing a first plunger through a first tube-shaped proximal portion of the first fluid tight bag into the distal end of the first fluid tight bag while the first substance is in a fluid state, and the step of introducing the second substance is implemented by pushing a second plunger through a second tube-shaped proximal portion of the second fluid tight bag into the distal end of the second fluid tight bag while the second substance is in a fluid state. In some embodiments, the method further includes the steps of withdrawing the first plunger via the first tube-shaped proximal portion after the first substance has solidified, and withdrawing the second plunger via the second tube-shaped proximal portion after the second substance has solidified. In some embodiments, the step of extending the distal end of the first fluid-tight bag includes extending the distal end of the first fluid-tight bag to a diameter of at least 2 cm, and the step of extending the distal end of the second fluid-tight bag includes extending the distal end of the second fluid-tight bag to a diameter of at least 2 cm. In some embodiments, the step of extending the distal end of the first fluid-tight bag includes extending the distal end of the first fluid-tight bag to a diameter between 3 and 6 cm, and the step of extending the distal end of the second fluid-tight bag includes extending the distal end of the second fluid-tight bag to a diameter between 3 and 6 cm.

DESCRIPTION OF THE PREFERRED EMBODIMENTS

Figure 1:
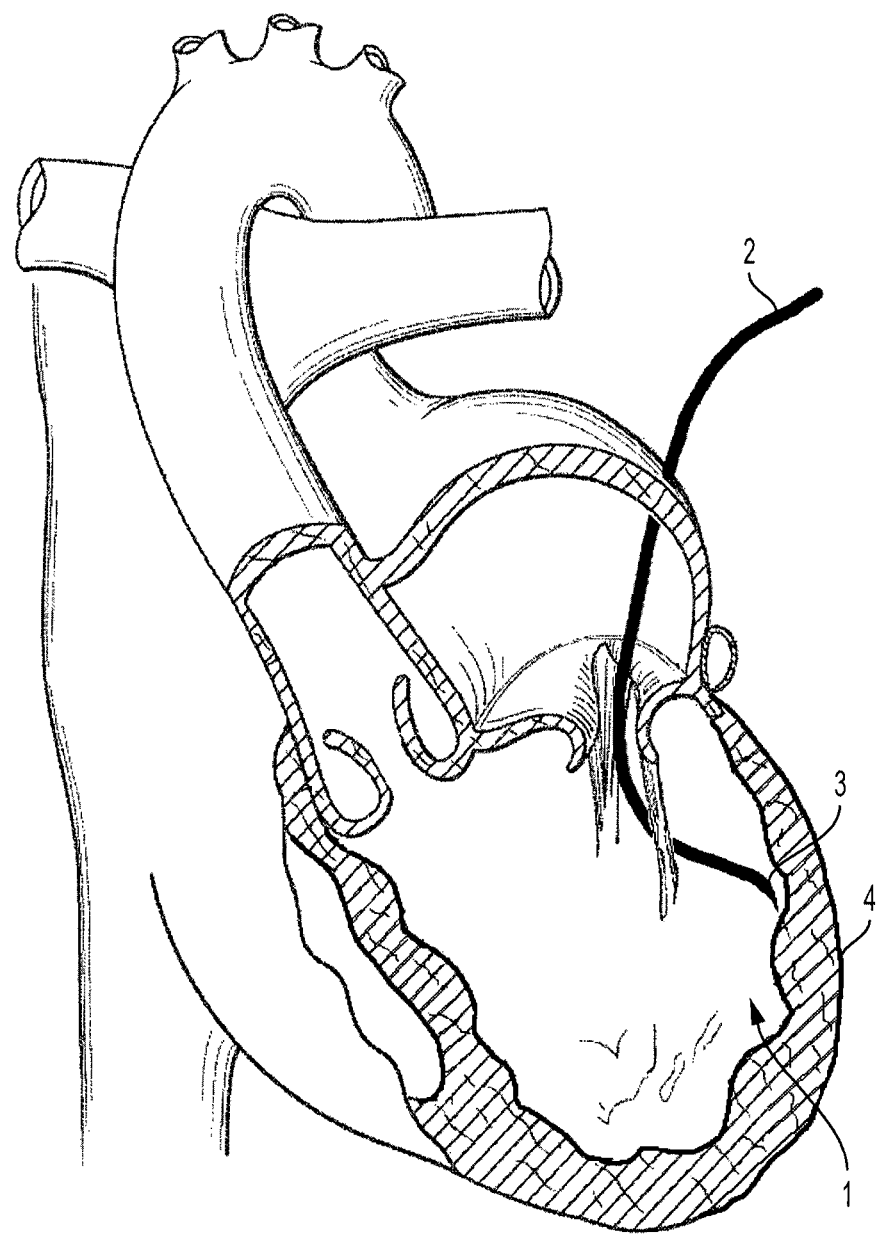
FIG. 1 shows a cross section of the left ventricle of a dilated heart, with a catheter percutaneously inserted to the left ventricle through the Mitral valve. The sharp catheter tip is positioned on the inner surface of the heart muscle wall.

FIG. 1 shows a cross section of the left ventricle 1 of a dilated heart. In this figure a catheter 2 is percutaneously inserted in the left ventricle through a puncture in the left atrium. But in alternative embodiments it is also possible to advance the catheter to the same location through the vascular system and through the Mitral valve. The catheter tip 3 is positioned on the inner surface of the heart muscle wall 4, and then advanced to puncture the heart muscle wall 4 from within. In some embodiments, the process of puncturing the heart muscle wall and passing a catheter through the puncture is done in gradual steps: first a very thin needle will be inserted through the heart muscle wall 4 and then a guide wire can be passed through the needle to serve as a rail, and over it bigger and bigger catheters can be advanced and inserted through the heart muscle wall 4 to dilate the puncture site until the desired puncture size is achieved.

After crossing the heart muscle wall 4 the catheter penetrates the space between other organs outside of the heart (typically under the pericardium) without puncturing through them. In some embodiments, the risk of puncturing the pericardium is minimized by using a relatively soft material (e.g., polyurethane or polyethylene) and by using a smooth surface at the tip of the catheter. The catheter itself also serves as a hemostasis plug as it fills the puncture site 5 and prevents bleeding from the puncture in the heart muscle wall 4. In some embodiments, the catheter may be passed through the heart muscle wall 4 at a shallow angle to further minimize the risk of bleeding.

Figure 2:
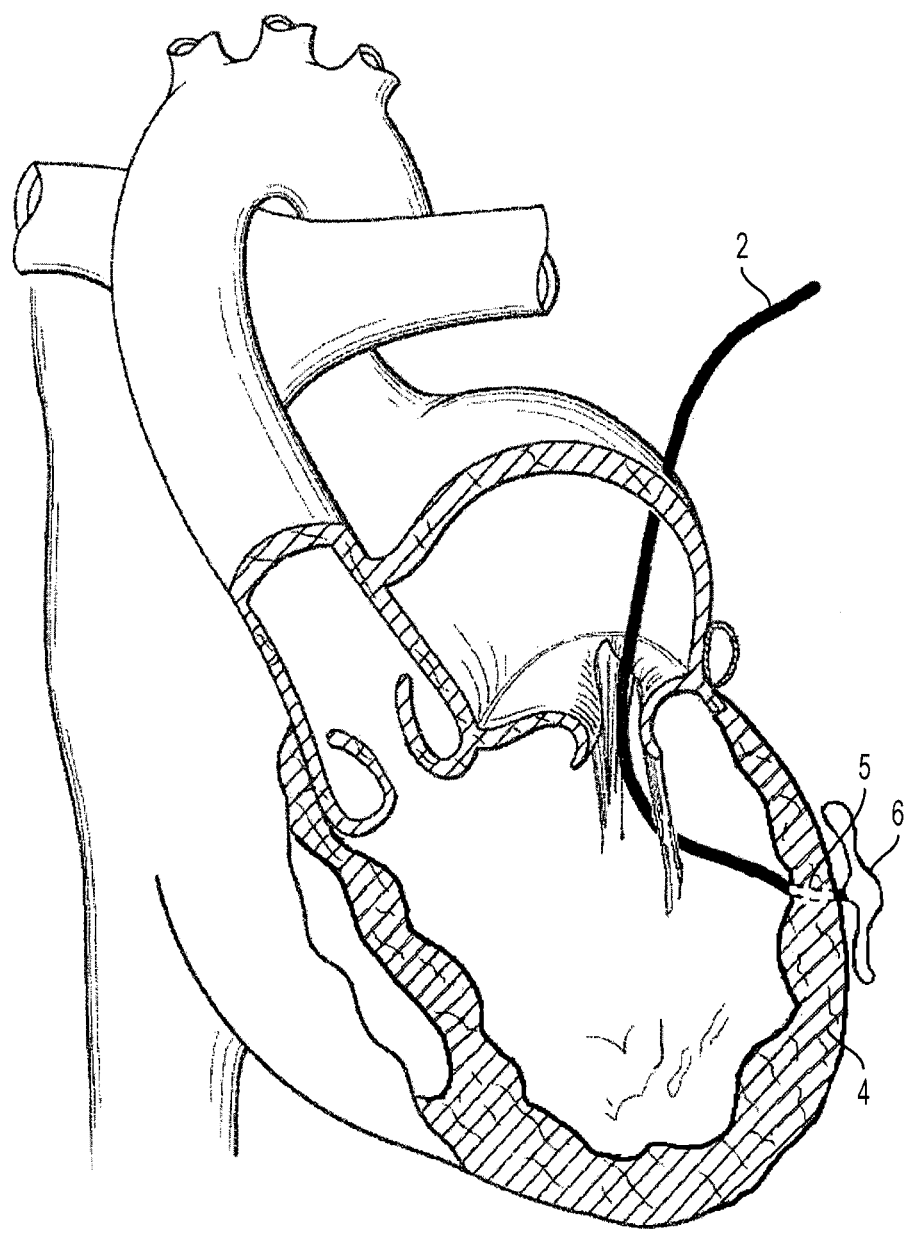
FIG. 2 shows the catheter tip after crossing the heart muscle wall through a puncture in it, and positioned outside of the heart. A thin material bag is being dispensed through the lumen of the catheter, and being unfolded and expanded outside of the heart.

FIG. 2 shows the catheter tip positioned outside of the heart after crossing the heart muscle wall through the puncture. At this stage a thin polymer bag 6 is dispensed through the lumen of the catheter, and is expanded outside of the heart. Preferably, the polymer bag 6 is expanded between the heart muscle wall 4 and the pericardium (although in alternative embodiments the polymer bag 6 may be expanded outside the pericardium).

Figure 8:
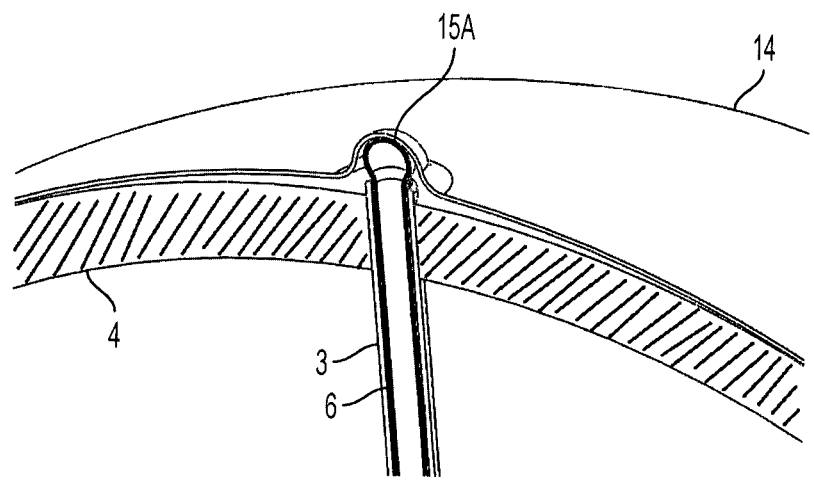
FIG. 8 shows a detail of how a polymer bag is dispensed through a catheter tip 3 to form a rounded protrusion.
Figure 9:
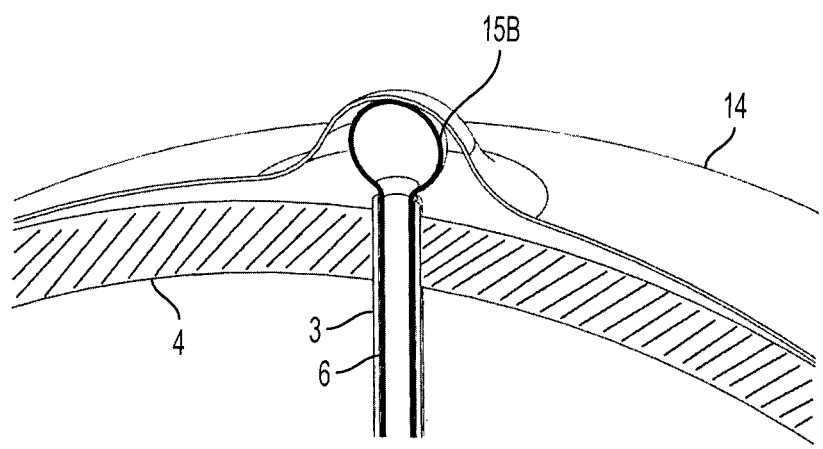
FIG. 9 shows a subsequent step for the embodiment of FIG. 8, in which the polymer bag has been further inflated to form a larger rounded protrusion.

FIGS. 8-12 show one approach for expanding the polymer bag 6 between the heart muscle wall 4 and the pericardium 14 in greater detail. In this embodiment, the spreading and expanding of the polymer bag 6 outside of the heart muscle wall 4 is accomplished by injecting saline or another liquid to the bag under pressure to inflate the bag like a small balloon. In FIG. 8, the polymer bag 6 is pushed and dispensed through a catheter tip 3 with aid of pressure of liquid like saline from within the polymer bag. The pressure causes the distal end of the polymer bag 6 to form a rounded protrusion 15A. As the polymer bag 6 is advanced in a distal direction, this rounded protrusion 15A pushes the pericardium 14 away from the heart muscle wall 4. As the internal pressure is increased and the polymer bag 6 is further advanced through the catheter tip, the rounded protrusion gets bigger, as depicted by the rounded protrusion 15B in FIG. 9.

Figure 10:
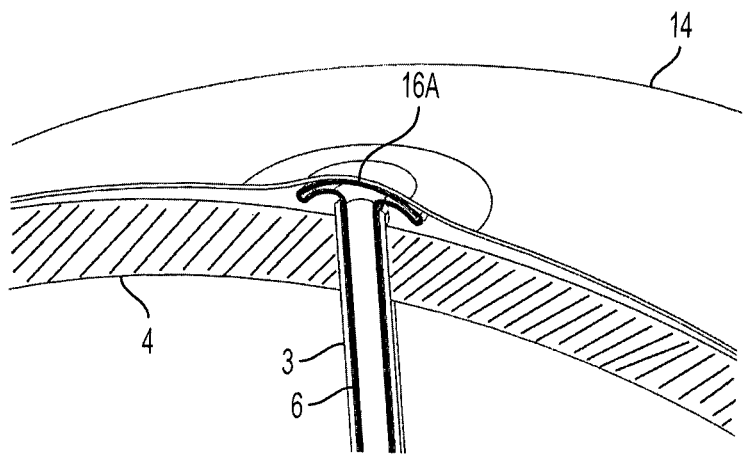
FIG. 10 shows a subsequent step for the embodiment of FIG. 8, in which the inflated polymer bag has been flattened into a mushroom shape beneath the pericardium.

At this point the internal pressure in the bag may be released, which causes the polymer bag 6 to collapse under the external tension of the pericardium 14 and other organs outside of the heart. When the polymer bag 6 collapses, the extra material flattens and spreads around the puncture site 5 and settles into a mushroom shape 16A beneath the pericardium 14 as shown in FIG. 10.

Figure 11:
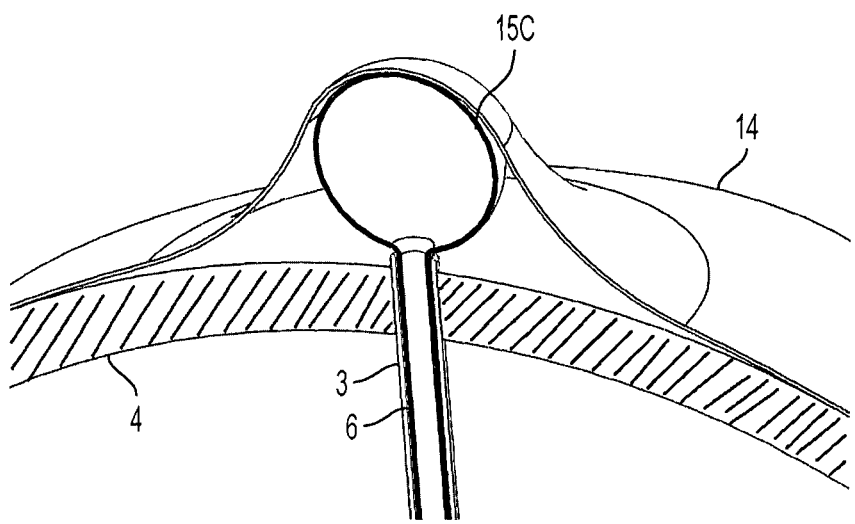
FIG. 11 shows a subsequent step for the embodiment of FIG. 8, in which the polymer bag has been re-inflated to form an even larger rounded protrusion.
Figure 12:
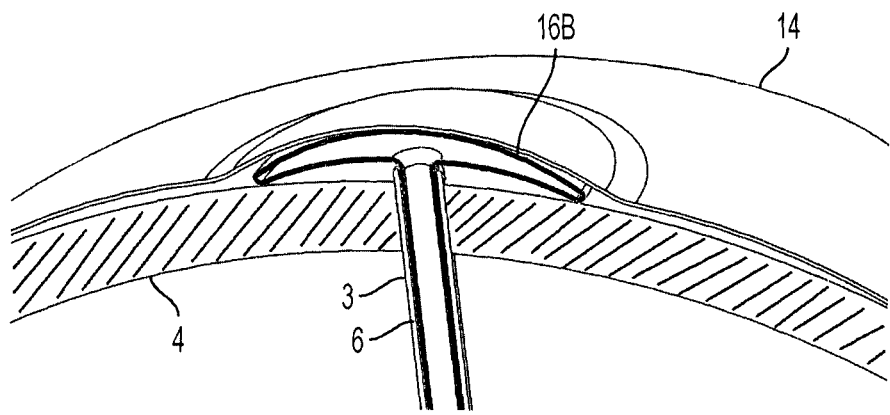
FIG. 12 shows a subsequent step for the embodiment of FIG. 8, in which the inflated polymer bag has been flattened into a larger mushroom shape beneath the pericardium.

Optionally, if the diameter of the mushroom shape 16A is not big enough, the process of inflating the bag and advancing it further through the catheter under pressure may be repeated. This results in an even bigger rounded protrusion 15C, as shown in FIG. 11. The internal pressure in the bag is then released a second time, which causes the polymer bag 6 to collapse and settle into a larger mushroom shape 16B beneath the pericardium 14 as shown in FIG. 12. Preferably, the mushroom shape 16B has a diameter of at least 2 cm, and preferably the diameter is less than 8 cm. More preferably, the diameter is between 3 and 6 cm.

In alternative embodiments (not shown), other approaches may be used to obtain the desired mushroom shape 16B at the distal end of the polymer bag 6 outside the heart muscle wall 4 and beneath the pericardium 14. For example, the polymer bag 6 may be expanded outside of the heart muscle wall 4 by dispensing a soft guide wire through the catheter and twisting the guide wire it in order to push the polymer bag around and expand it to the desired mushroom shape.

During this process, at least one opened lumen connects operating features (like various liquid syringes or pumps) outside of the body through the catheter 2 to the thin wall polymer bag 6, which allows inflation and deflation of the bag with liquids such as saline.

After the polymer bag 6 has been expanded to the desired mushroom shape 16B between the heart muscle wall 4 and the pericardium 14, the saline (or other inert liquid) is pumped out. A fluid that is designed to solidify is then pumped into the polymer bag 6 in order to form a mushroom shape pad 7. In some embodiments, the fluid is a mixture of A and B components of implantable grade thermosetting polymer like Epoxy, Urethane, or Acrylic. The A and B components are preferably mixed together outside the body immediately before being injected into the polymer bag 6, and the pressure is maintained so that the distal end of the polymer bag 6 inflates with the fluid and remains inflated. The solidification time for such polymers can be from a few minutes to half an hour, depending on the particular polymer that is used. After the fluid solidifies, the result will be a solid filler material disposed inside the polymer bag 6, with a mushroom shaped distal end that preferably has a diameter of at least 2 cm. Preferably the diameter is less than 8 cm. More preferably, the diameter is between 3 and 6 cm.

In alternative embodiments, the A and B components may be injected into the polymer bag 6 separately, via separate lumens (not shown) in the catheter 2. When two lumens are used, either the A or B component may optionally be used in place of the saline described above in the preliminary steps of inflating the polymer bag 6 to its desired shape. In this case, the first component is used to inflate the polymer bags 6 to the desired shape in the intended location, and then the other component is added through the other lumen to initiate the chemical solidifying reaction.

In other embodiments, alternative approaches for solidifying the fluid are used, including but not limited to thermally cured liquids that are cured into solids using either body heat from the patient or externally applied heat, liquids that are cured into solids when electromagnetic energy is applied, and liquids that are cured into solids when ultrasound energy is applied.

Figure 3:
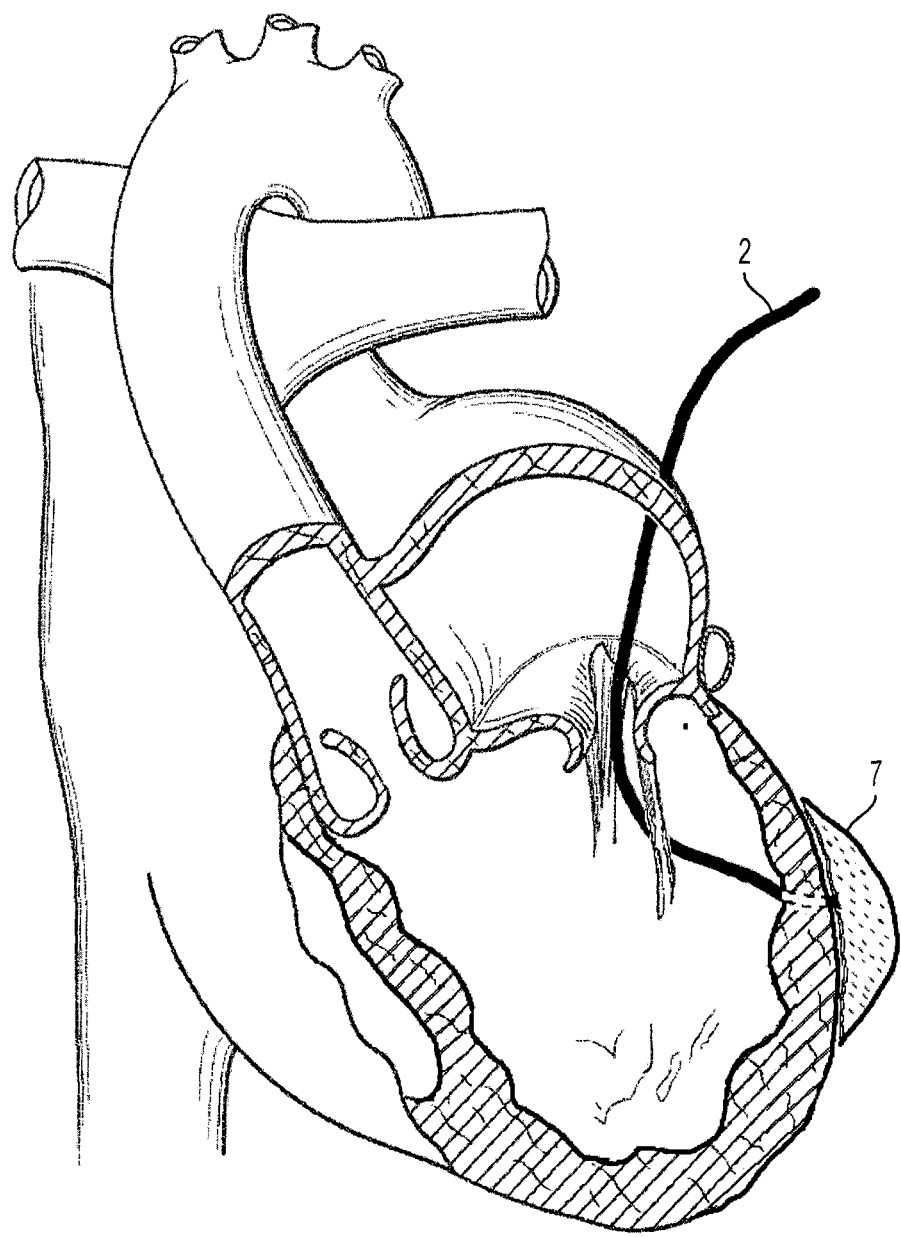
FIG. 3 shows a cross section of the left ventricle with the thin material bag outside of the heart muscle wall after being inflated to a shape of a mushroom with fluid that can be solidified, typically thermosetting polymer.

FIG. 3 shows a cross section of the left ventricle with the thin material bag outside of the heart muscle wall 4 after the mushroom shape pad 7 has been formed.

Figure 4:
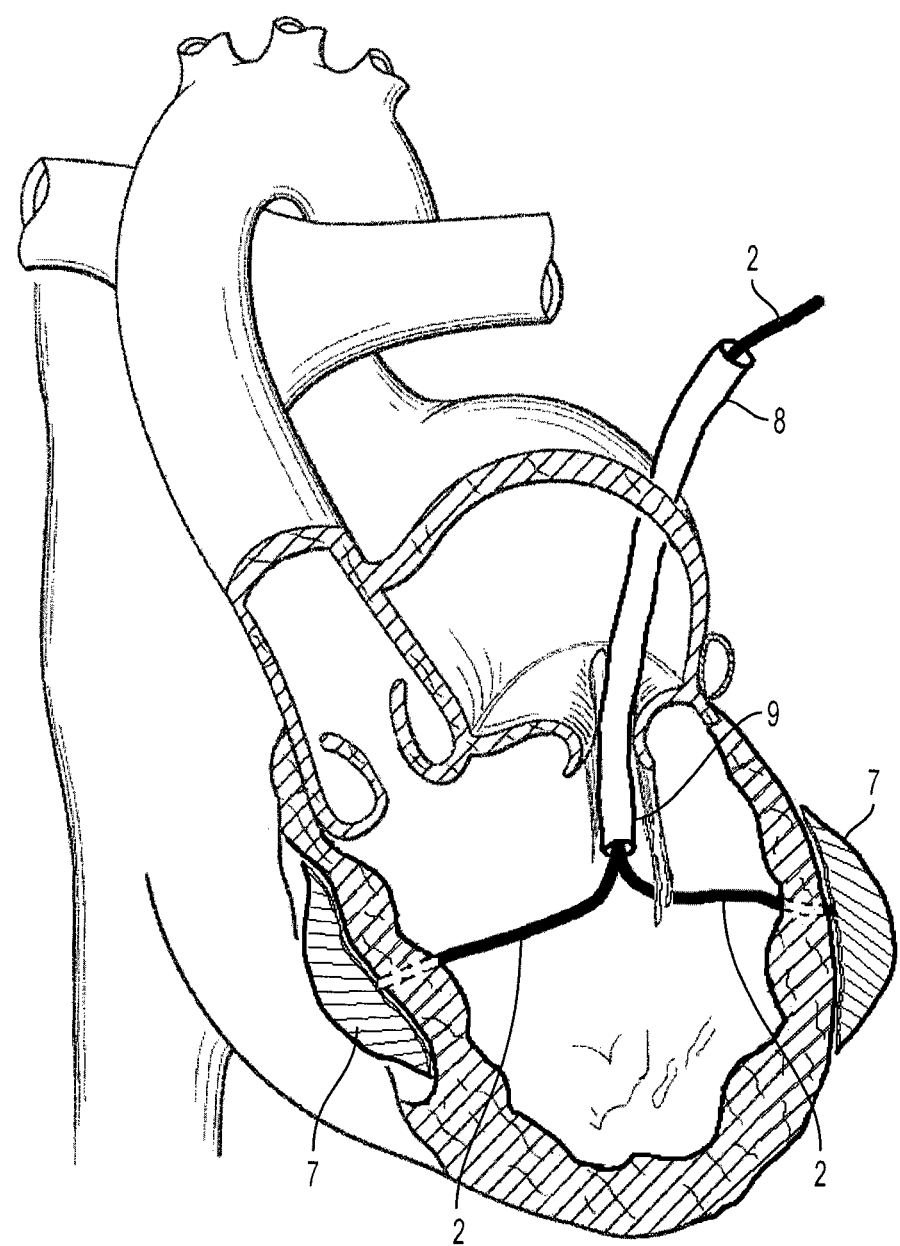
FIG. 4 shows a cross section of the left ventricle with two thin material bags outside of the heart opposing one another, after the fluid has inflated the bags to the shape of a mushroom and has been solidified. The two bags become structural pads still connected to the delivery catheters within the heart.

FIG. 4 shows a cross section of the left ventricle after the process described above in connection with FIGS. 1-3 has been repeated to form a second mushroom shape pad 7 on the opposite side of the heart from the first mushroom shape pad 7. At this stage of the procedure a sleeve 8 is advanced over the two catheters 2 until the distal end 9 of the sleeve 8 reaches a point within the left ventricle typically right between the two pads 7. The sleeve 8 is non-compressible in the proximal-to-distal direction, and is made of any suitable biocompatible non-compressible material such as Nylon with a metal braided reinforcement.

Note that the mushroom shape pads 7 are still connected to the delivery catheters 2 located within the heart. Since the polymer bag (typically urethane) will be enveloping the pad before and after solidification, the mushroom shape pads 7 will remain connected to the catheters 2, so that pulling inwards on the catheters 2 will pull the mushroom shape pad 7 inward.

Figure 5:
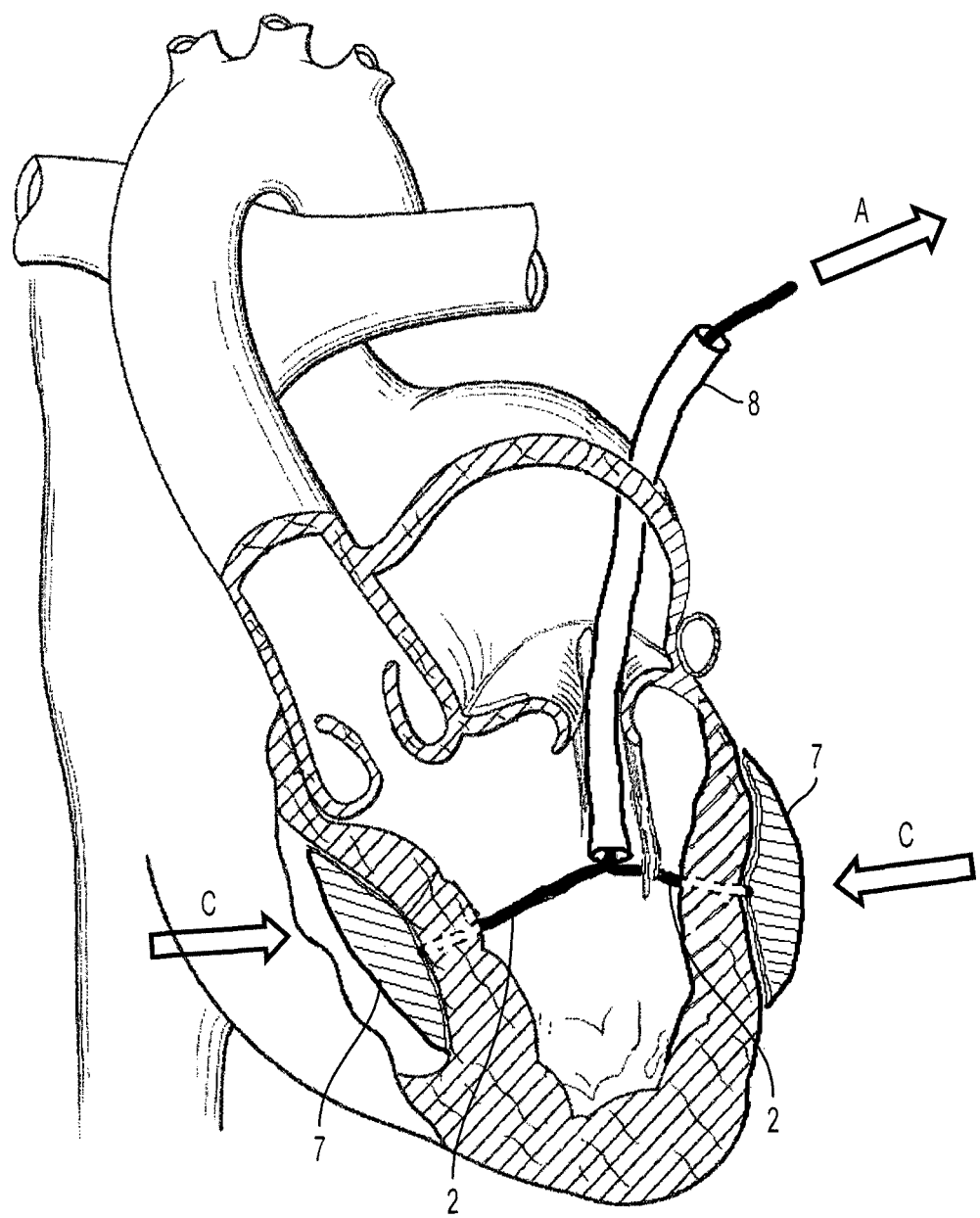
FIG. 5 shows a cross section of the left ventricle as the heart walls are being pulled from within towards each other by the catheters that serve as tethers.

FIG. 5 shows how by pulling the catheters 2 that are still attached to the mushroom shape pads 7 pads while holding the sleeve 8 still (or, alternatively, while pushing the sleeve 8 in a distal direction), the two mushroom shape pads 7 are pulled towards one another from within the heart. This pulling action draws the ventricle walls towards one another, thereby reshaping the left ventricle 1. In alternative embodiments, a similar procedure can be done with three or more mushroom shaped pads 7 in a similar manner. In these embodiments, the location, number, and shape of the pads may be determined by the physician to obtain the optimal reshaping of the ventricle.

After the desired reshaping has been obtained, a locking mechanism such as a clip is advanced over the catheters to permanently lock the catheters to each other. In alternative embodiments, the catheters may be locked together using one-way connectors with a ratcheting action, by making a knot, twisting the ends of the catheters together, etc. The proximal end of the catheters is then removed while the distal ends of the catheters remain inside the ventricle and remain connected to the mushroom shaped pads 7 outside of the heart to maintain the reshaped ventricle under constant tension.

Figure 6:
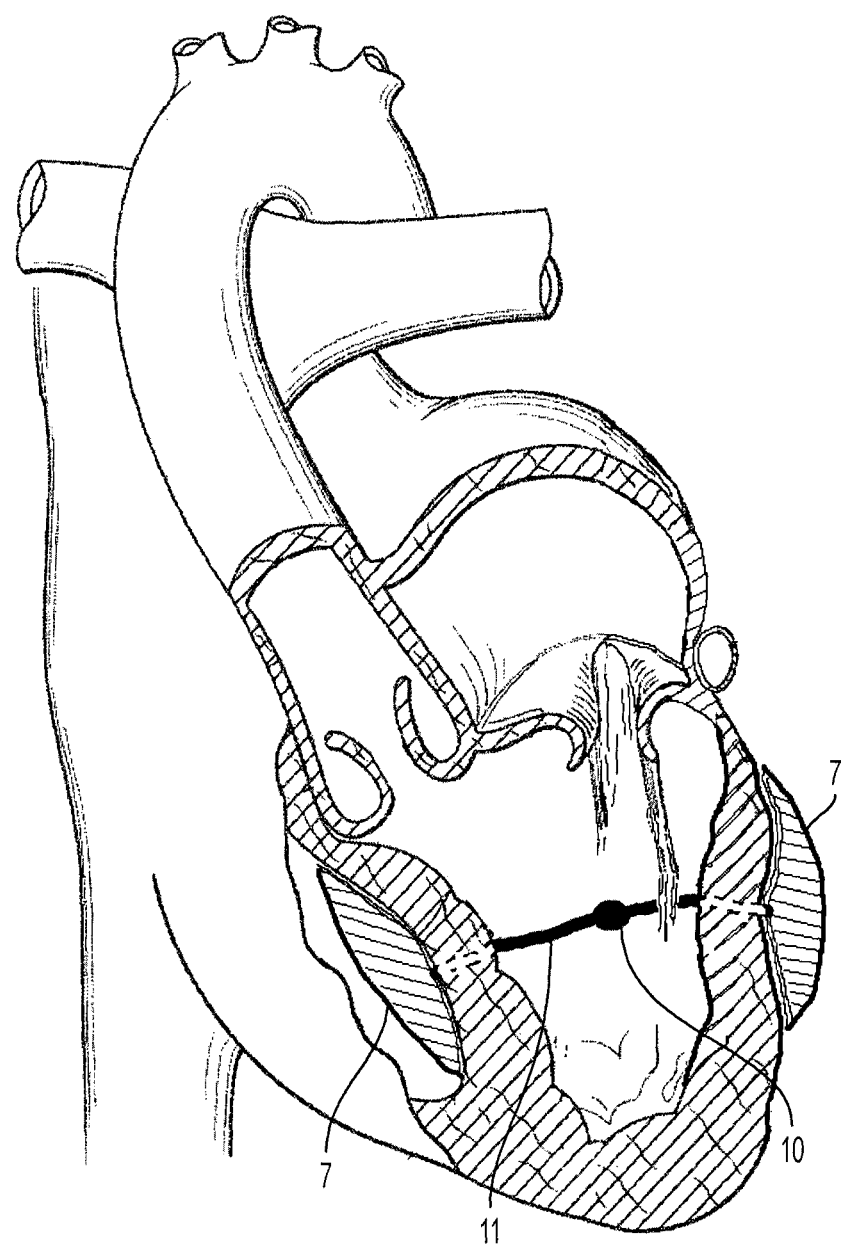
FIG. 6 shows a cross section of the left ventricle after the heart walls have been pulled from within; the distal ends of the catheters have been attached together permanently and the proximal ends have been removed.

FIG. 6 shows the final step of the procedure in a cross section of the left ventricle after the heart walls have been pulled towards each other from within. At this stage the distal ends of the catheters are attached together permanently by the locking mechanism such as a mechanical clip 10 or by another approach, and the proximal ends have been removed. Note that when solidified fluid remains in the distal ends of the catheters, the catheters lumen will be rigid and act like a rod 11. In this embodiment, the attached catheters serve as an elongated member, and this elongated member is attached to the solid filler material in each of the mushroom shape pads 7 via the intervening polymer bag 6.

In alternative embodiments when no solidified fluid remains in the distal ends of the catheters, the distal ends of the catheters may remain flexible and act like a tether. In other alternative embodiments, the ventricle walls may be pulled together by cords or tethers, as separate members from the catheters that served to inflate the pads as described above. In other alternative embodiments, the proximal portion of the polymer bag 6 itself may be used to pull the mushroom shape pads 7 towards each other, as described below in connection with FIGS. 13-19.

Figure 7:
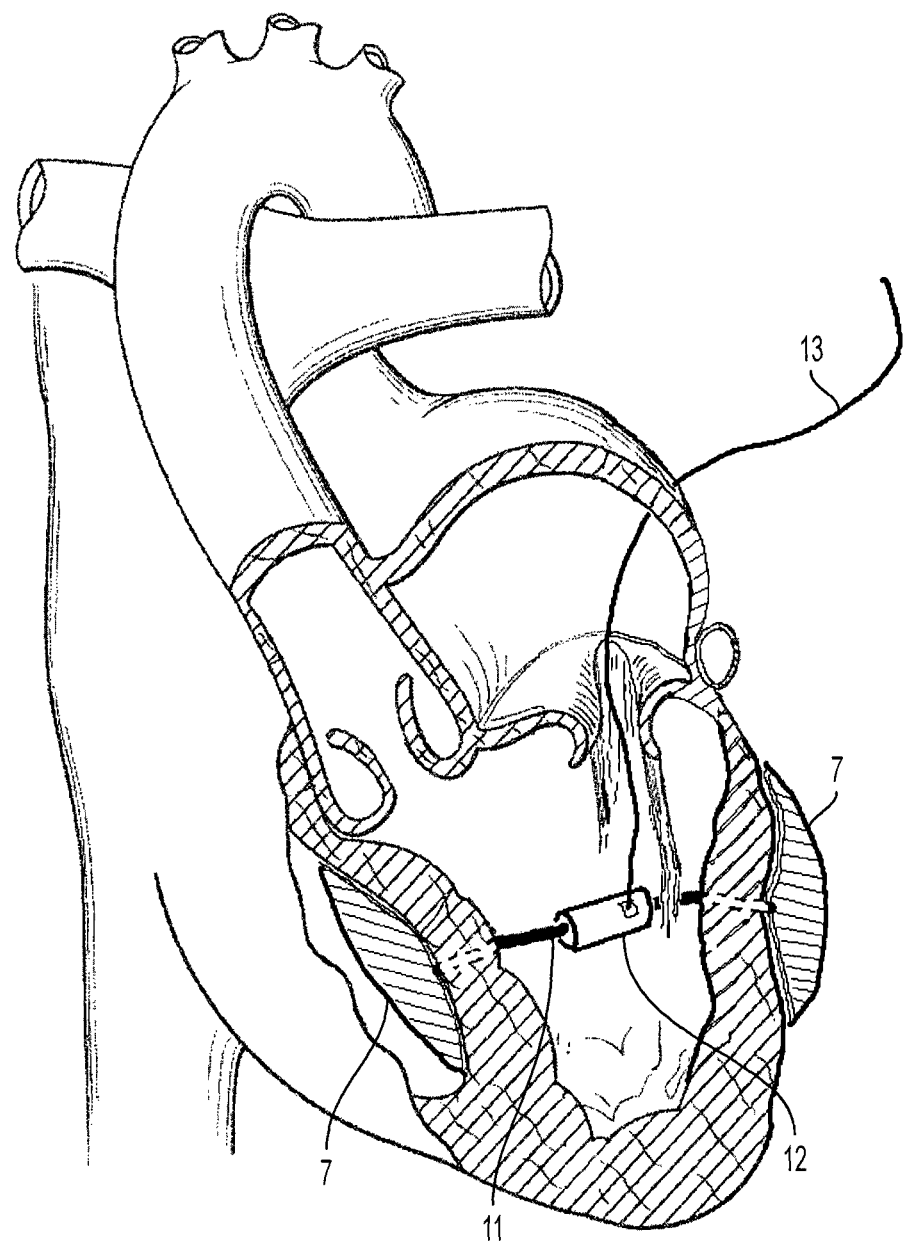
FIG. 7 shows another embodiment of the invention in which a small mechanical actuator is placed within the heart ventricle and attached to the pads.

FIG. 7 shows another embodiment of the invention in which, instead of connecting the two mushroom shape pads 7 directly together (e.g., using the catheters, cords, tethers, rods, or another approach), a small mechanical actuator 12 is placed within the heart ventricle and attached to both of the mushroom shaped pads 7. In this embodiment the mechanical actuator pulls the mushroom shape pad 7 towards one another continuously in cyclic manner, thereby causing the left ventricle to contract and expand, effectively acting like a dynamic heart assist device. The mechanical actuator can be placed in the ventricle through the wall of the left atrium or through the vascular system after the mushroom shaped pads 7 had been placed, and remain suspended within the ventricle by the tension of the cords or rods 11, attached to the mushroom shape pad 7. The actuator can be powered electrically or by other source of external energy supplied through thin wires 13 that run from a battery outside of the body through the atrium wall or vascular system, passing between the commissures of the Mitral valve leaflets.

FIGS. 13-19 depict another embodiment that is similar to the embodiment of FIGS. 8-12. But in the FIG. 13-19 embodiment, instead of relying on the catheters themselves to hold the two mushroom shaped structural pads 7 together, the proximal tube-shaped portion of the polymer bag 6 is used for this purpose. In this embodiment, the bag is expanded outside the heart muscle wall 4 and beneath the pericardium 14 by injecting saline or another liquid into the bag under pressure to inflate the bag, as described above in connection with FIGS. 8-12. After the polymer bag 6 has been expanded to the desired mushroom size and shape, the saline (or other inert liquid) is pumped out to evacuate the polymer bag 6.

A desired quantity of solidifying fluid 20 is then introduced into the proximal opening of the polymer bag 6 in a fluid state and a plunger 25 is then pushed through the tube shaped portion proximal portion of the polymer bag 6 to push the solidifying fluid 20 distally. The plunger 25 is advanced until the plunger 25 reaches the vicinity of the heart muscle wall 4. The plunger is preferably pushed through the tube shaped portion proximal portion of the polymer bag 6 using a push wire 27. The plunger 25 is preferably made of a rigid material that does not bond to the solidifying fluid 20 after it has solidified. Suitable examples of material for the plunger 25 include Teflon, polyethylene, and metals coated with Teflon or similar materials. The plunger 25 is preferably sized to accommodate the walls of the tube shaped portion of the polymer bag 6 that run through the catheter 2 so that zero or very little solidifying fluid 20 will remain attached to the walls of the polymer bag 6 after the plunger has moved past.

Figure 13:
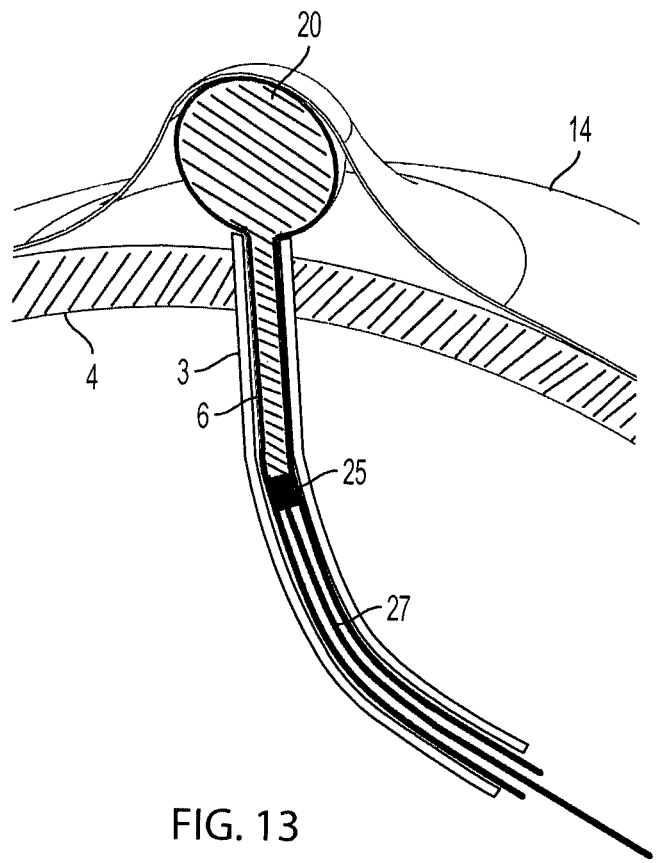
FIG. 13 shows a detail of another embodiment in which a polymer bag is filled with a solidifying fluid using a plunger.
Figure 14:
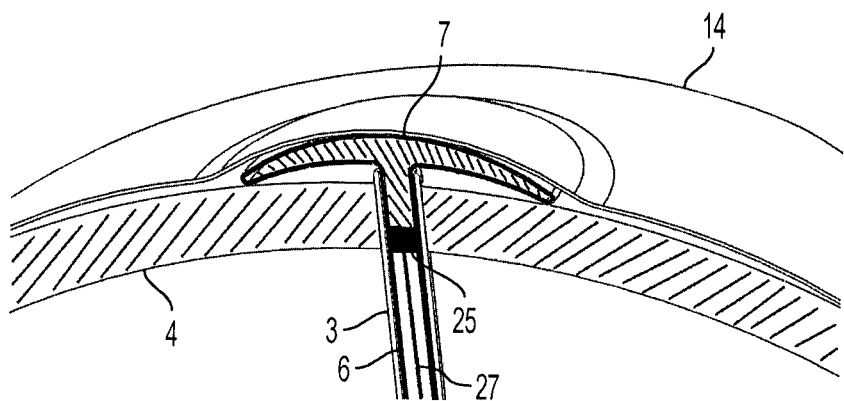
FIG. 14 shows a subsequent step for the embodiment of FIG. 13, in which the plunger has been pushed to its distalmost position.

The quantity of solidifying fluid 20 that is introduced into the polymer bag 6 is preferably selected so that when the plunger 25 reaches the vicinity of the heart muscle wall 4, the quantity of solidifying fluid 20 that will have been forced into the distal end of the polymer bag 6 will eventually solidify into a mushroom shape pad 7 of the desired size (e.g., greater than 2 cm, 2-8 cm, or more preferably 3-6 cm in diameter, as described above). For example, about 2 cc is needed to form a pad with a diameter of 2 cm; about 7 cc is needed to form a pad with diameter of 3 cm; and about 40 cc is needed to form a pad with a diameter of 6 cm. Initially, while the solidifying fluid 20 is being forced into the distal end of the polymer bag 6, the solidifying fluid 20 may cause the distal end of the polymer bag 6 to bulge outward as seen in FIG. 13. But the pericardium 14 will compress the solidifying fluid 20 into the desired mushroom shape seen in FIG. 14 before the fluid solidifies. The plunger 25 is preferably held in its position near the heart muscle wall 4 until the solidifying fluid 20 has completely solidified into a solid filler material, which forms the mushroom shaped pad 7 depicted in FIG. 14.

Figure 15:
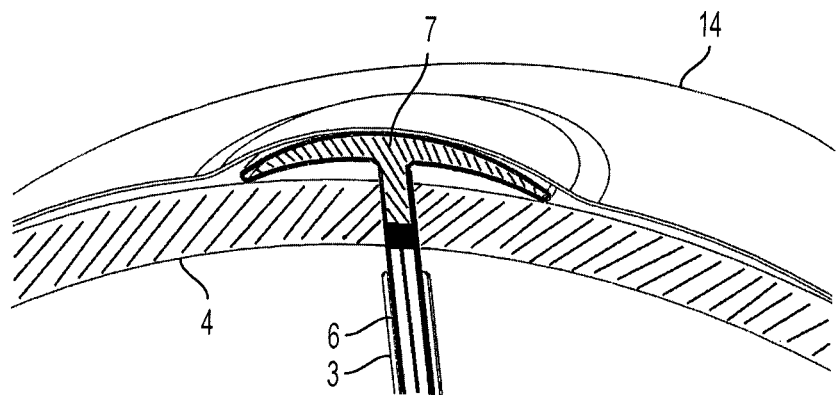
FIG. 15 shows a subsequent step for the embodiment of FIG. 13, in which the catheter is being withdrawn.

Note that when the mushroom shape pads 7 are formed outside of the heart muscle wall 4, a seal is initially maintained on the puncture in the wall of the ventricle by the catheter tip 3 to prevent blood loss during the procedure. After the solidifying fluid 20 has solidified, the catheter tip 3 is withdrawn, as shown in FIG. 15, and the solid mushroom shape pad 7 will act like a plug and maintain the seal.

Figure 16:
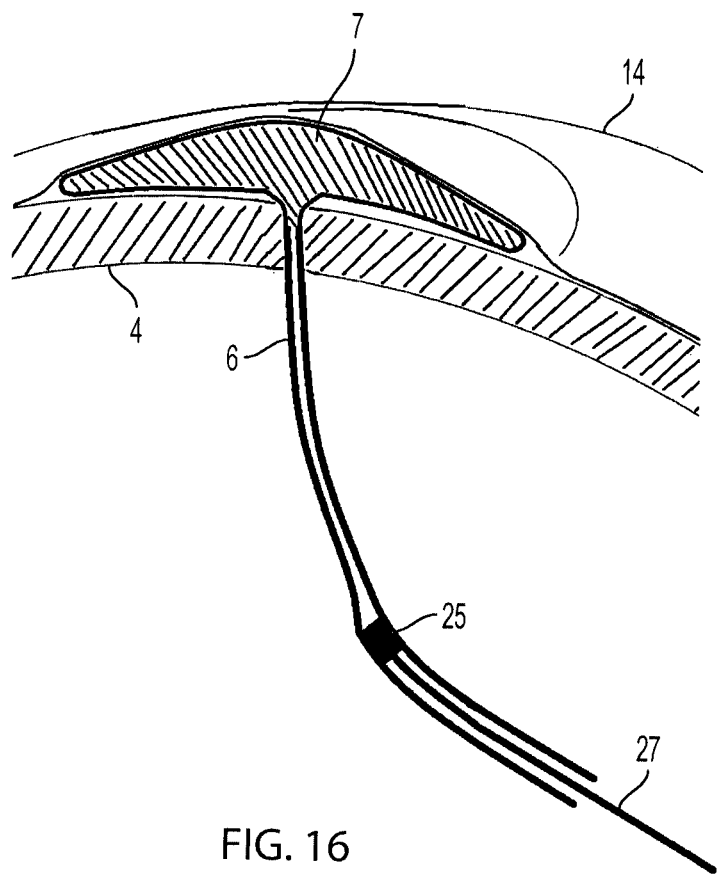
FIG. 16 shows a subsequent step for the embodiment of FIG. 13, in which the plunger is being withdrawn.

The plunger 25 is then withdrawn in a proximal direction by pulling on the pull wire 27 that is attached to the plunger 25. Because no (or very little) solidifying fluid 20 remains on the walls of the tube shaped portion of the polymer bag 6, it will be possible to retract the plunger 25 through the tube-shaped proximal portion of the polymer bag 6, as seen in FIG. 16. Note that the time sequence of the withdrawal of the catheter 3 and the withdrawal of the plunger 25 is not critical, and that the sequence of those two steps may be reversed in some embodiments.

Figure 17:
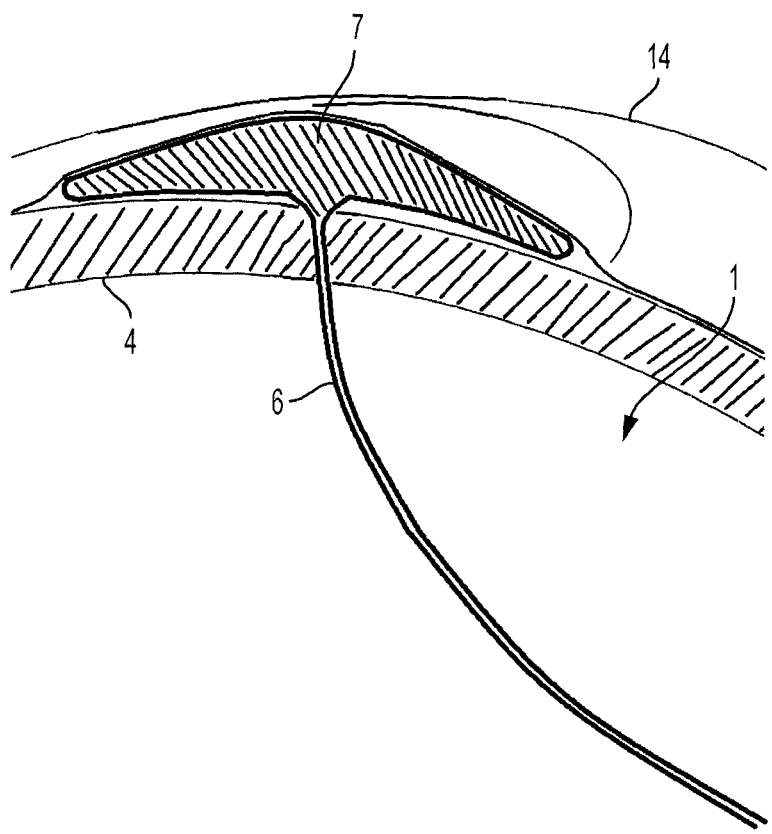
FIG. 17 shows a subsequent step for the embodiment of FIG. 13, after the plunger has been completely withdrawn.

After the plunger 25 has been fully withdrawn, the mushroom shaped structural pad 7 will preferably be positioned as it appears in FIG. 17, disposed outside the heart muscle wall 4 and beneath the pericardium 14, with the tube shaped proximal portion of the polymer bag 6 hanging into the ventricle 1.

Figure 18:
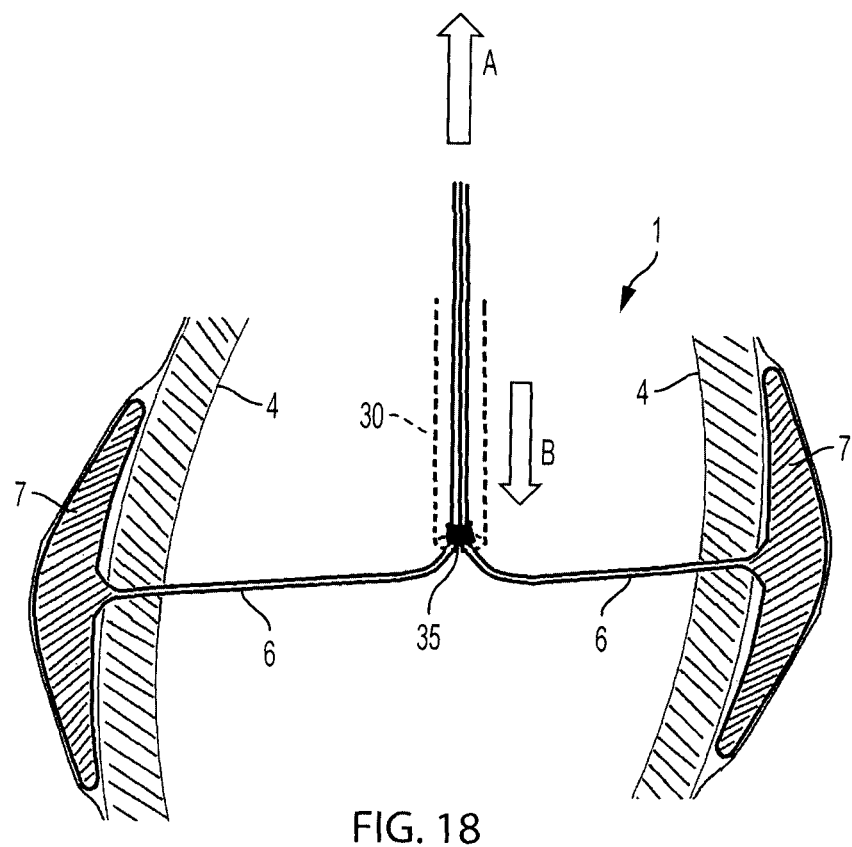
FIG. 18 shows a subsequent step for the embodiment of FIG. 13, in which the mushroom shape pads are being connected.

The same process is then repeated on the opposite side of the ventricle 1 to form a second mushroom shaped structural pad 7. After both mushroom shaped structural pads 7 have been installed beyond the heart muscle wall heart muscle wall 4, with the proximal portion of both polymer bags 6 hanging into the ventricle, a push sleeve 30 is advanced over both proximal portions of the polymer bags 6, as shown in FIG. 18. Pushing on the push sleeve 30 in the direction of arrow B while pulling on the proximal ends of the polymer bag 6 in the direction of arrow A will pull the two mushroom shaped structural pads 7 towards each other. A clip 35 or other fastener is then installed at the junction point between the proximal portions of the two polymer bags 6 that were previously hanging into the ventricle 1, to join those two proximal portions together under tension.

Figure 19:
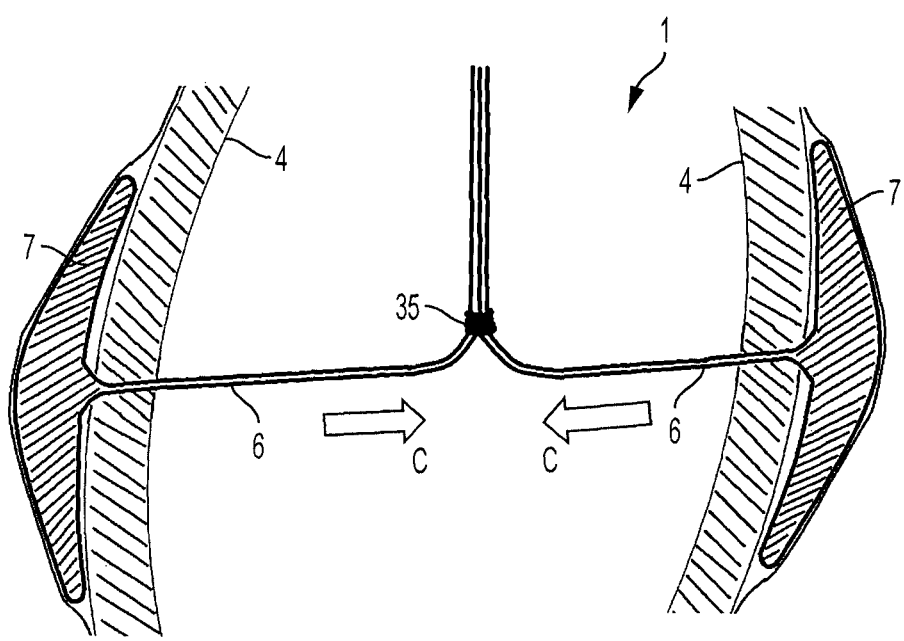
FIG. 19 shows a subsequent step for the embodiment of FIG. 13, after the mushroom shape pads have been connected.

At this point, the push sleeve 30 is removed, resulting in the configuration shown in FIG. 19. The clip 35 and the portions of the polymer bags 6 that are distal to the clip 35 will then pull both of the mushroom shaped structural pads 7 towards each other in the direction of arrow C, which will reshape the ventricle. The portions of the tube-shaped portion of the polymer bag 6 that are proximal to the clip 35 can then be removed, at which point the procedure is complete. In this embodiment, the attached portions of the tube-shaped portion of the polymer bag 6 that are proximal to the clip 35 serve as an elongated member, and this elongated member is attached to the solid filler material in each of the mushroom shape pads 7 because the pads are disposed inside the distal end of the polymer bag 6.

Figure 20:
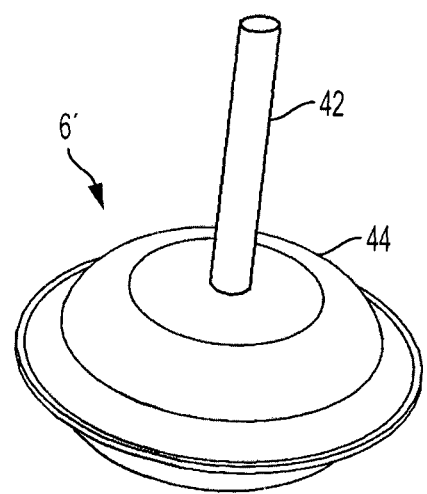
FIG. 20 shows an alternative configuration for the distal end of the polymer bag.

FIG. 20 depicts an alternative configuration 6' for the distal end of the polymer bag, which may be used in conjunction with any of the embodiments described above. In this configuration, instead of using the bag 6 with a uniform structure, as described above in connection with FIGS. 8-20, The bag 6' of this embodiment has a long tube-shaped portion 42 connected to a mushroom shaped section 44 disposed at the distal end of the polymer bag 6'. The interior of the tube-shaped portion 42 is in fluid communication with the interior of the mushroom shaped section 44, so that the mushroom shaped section 44 can be filled through the tube-shaped portion 42. When this configuration is used, the steps of injecting saline (or another inert liquid) should be repeated until the entire mushroom shaped section 44 has been delivered beyond the heart muscle wall and beneath the pericardium 14. The mushroom shaped section 44 is then filled with the solidifying fluid 20, in a manner similar to the embodiments described above.

While the present invention has been disclosed with reference to certain embodiments, numerous modifications, alterations, and changes to the described embodiments are possible without departing from the spirit and scope of the present invention, as defined in the appended claims. Accordingly, it is intended that the present invention not be limited to the described embodiments, but that it has the full scope defined by the language of the following claims, and equivalents thereof.

I claim:

1. An apparatus for reshaping a ventricle of a heart, the ventricle having a first wall section and a second wall section that is disposed opposite to the first wall section, the apparatus comprising:
    a first fluid-tight bag having a first inlet that is configured to accept a fluid and a distal end that is configured to pass through a first hole in the first wall section and extend outside the ventricle, wherein the first fluid-tight bag is configured so that when the distal end of the first fluid-tight bag has passed through the first hole and has been extended outside the ventricle, at least a portion of the distal end of the first fluid-tight bag that extends outside the ventricle has a diameter that is larger than the first hole;
    a first solid filler material disposed outside the ventricle in the distal end of the first fluid-tight bag, the first solid filler material having a diameter that is larger than the first hole, wherein the first solid filler material is formed by introducing at least one fluid substance into the first fluid-tight bag via the first inlet after the distal end of the first fluid-tight bag has passed through the first hole and has been extended outside the ventricle, wherein the at least one fluid substance is configured to solidify after being introduced into the first fluid-tight bag;
    a second fluid-tight bag having a second inlet that is configured to accept a fluid and a distal end that is configured to pass through a second hole in the second wall section and extend outside the ventricle, wherein the second fluid-tight bag is configured so that when the distal end of the second fluid-tight bag has passed through the second hole and has been extended outside the ventricle, at least a portion of the distal end of the second fluid-tight bag that extends outside the ventricle has a diameter that is larger than the second hole;
    a second solid filler material disposed outside the ventricle in the distal end of the second fluid-tight bag, the second solid filler material having a diameter that is larger than the second hole, wherein the second solid filler material is formed by introducing at least one fluid substance into the second fluid-tight bag via the second inlet after the distal end of the second fluid-tight bag has passed through the second hole and has been extended outside the ventricle, wherein the at least one fluid substance is configured to solidify after being introduced into the second fluid-tight bag; and
    an elongated member having a first end and a second end, wherein the first end of the elongated member is attached to the first solid filler material and the second end of the elongated member is attached to the second solid filler material, wherein the elongated member is configured to pull the first solid filler material towards the second solid filler material, wherein the elongated member comprises a first section of catheter that is attached to the first solid filler material and a second section of catheter that is attached to the second solid filler material, and wherein the first section of the catheter is attached to the second section of the catheter.

2. The apparatus of claim 1, wherein the first fluid-tight bag has a first tube-shaped proximal portion that is connected to the distal end of the first fluid-tight bag, and wherein the second fluid-tight bag has a second tube-shaped proximal portion that is connected to the distal end of the second fluid-tight bag.

3. The apparatus of claim 2, wherein the elongated member is formed by attaching the first tube-shaped proximal portion to the second tube-shaped proximal portion.

4. The apparatus of claim 1, wherein the elongated member comprises a first section of tubing that is attached to the first solid filler material and a second section of tubing that is attached to the second solid filler material, and wherein the first section of tubing is attached to the second section of tubing.

5. The apparatus of claim 1, wherein the first solid filler material has a diameter of at least 2 cm and wherein the second solid filler material has a diameter of at least 2 cm.

6. The apparatus of claim 1, wherein the first solid filler material has a diameter between 3 and 6 cm and wherein the second solid filler material has a diameter between 3 and 6 cm.

7. An apparatus for reshaping a ventricle of a heart, the ventricle having a first wall section and a second wall section that is disposed opposite to the first wall section, the apparatus comprising:
 a first catheter configured to pass from inside the ventricle to outside the ventricle through a first hole in the first wall section, the first catheter having a first lumen;
 a first fluid-tight bag having a first inlet that is configured to accept a fluid and a distal end that is configured to pass through the first lumen and through the first hole in the first wall section and extend outside the ventricle, wherein the first fluid-tight bag is configured so that when the distal end of the first fluid-tight bag has passed through the first hole and has been extended outside the ventricle, at least a portion of the distal end of the first fluid-tight bag that extends outside the ventricle has a diameter that is larger than the first hole;
 a first substance configured for introduction into the first fluid-tight bag in a fluid state via the first inlet after the distal end of the first fluid-tight bag has passed through the first hole and has been extended outside the ventricle, wherein the first substance is configured to solidify after being introduced into the first fluid-tight bag;
 a second catheter configured to pass from inside the ventricle to outside the ventricle through a second hole in the second wall section, the second catheter having a second lumen;
 a second fluid-tight bag having a second inlet that is configured to accept a fluid and a distal end that is configured to pass through the second lumen and through the second hole in the second wall section and extend outside the ventricle, wherein the second fluid-tight bag is configured so that when the distal end of the second fluid-tight bag has passed through the second hole and has been extended outside the ventricle, at least a portion of the distal end of the second fluid-tight bag that extends outside the ventricle has a diameter that is larger than the second hole;
 a second substance configured for introduction into the second fluid-tight bag in a fluid state via the second inlet after the distal end of the second fluid-tight bag has passed through the second hole and has been extended outside the ventricle, wherein the second substance is configured to solidify after being introduced into the second fluid-tight bag; and
 an elongated member adapted to pull the first substance towards the second substance after the first substance and the second substance have solidified.

8. The apparatus of claim 7, wherein the first fluid-tight bag has a first tube-shaped proximal portion that is connected to the distal end of the first fluid-tight bag, and wherein the second fluid-tight bag has a second tube-shaped proximal portion that is connected to the distal end of the second fluid-tight bag.

9. The apparatus of claim 7, wherein the elongated member is formed by attaching the first tube-shaped proximal portion to the second tube-shaped proximal portion.

10. The apparatus of claim 7, further comprising a first plunger configured to push the first substance through the first tube-shaped proximal portion into the distal end of the first fluid-tight bag while the first substance is in a fluid state, and a second plunger configured to push the second substance through the second tube-shaped proximal portion into the distal end of the second fluid-tight bag while the second substance is in a fluid state.

11. The apparatus of claim 10, wherein the first plunger is further configured to facilitate withdrawal of the first plunger via the first tube-shaped proximal portion after the first substance has solidified, and wherein the second plunger is further configured to facilitate withdrawal of the second plunger via the second tube-shaped proximal portion after the second substance has solidified.

12. The apparatus of claim 7, wherein the elongated member comprises (a) a section of the first catheter and (b) a section of the second catheter that is connected to the section of the first catheter.

13. The apparatus of claim 7, wherein the first fluid-tight bag is configured so that when the distal end of the first fluid-tight bag has passed through the first hole and has been extended outside the ventricle, at least a portion of the distal end of the first fluid-tight bag that extends outside the ventricle has a diameter of at least 2 cm, and wherein the second fluid-tight bag is configured so that when the distal end of the second fluid-tight bag has passed through the second hole and has been extended outside the ventricle, at least a portion of the distal end of the second fluid-tight bag that extends outside the ventricle has a diameter of at least 2 cm.

14. The apparatus of claim 7, wherein the first fluid-tight bag is configured so that when the distal end of the first fluid-tight bag has passed through the first hole and has been extended outside the ventricle, at least a portion of the distal end of the first fluid-tight bag that extends outside the ventricle has a diameter between 3 and 6 cm, and wherein the second fluid-tight bag is configured so that when the distal end of the second fluid-tight bag has passed through the second hole and has been extended outside the ventricle, at least a portion of the distal end of the second fluid-tight bag that extends outside the ventricle has a diameter between 3 and 6 cm.

15. A method for reshaping a ventricle of a heart, the ventricle having a first wall section and a second wall section that is disposed opposite to the first wall section, the method comprising the steps of:
 passing a first catheter having a first lumen from inside the ventricle to outside the ventricle through a first hole in the first wall section;
 delivering, through the first catheter, a first fluid-tight bag having a first inlet that is configured to accept a fluid and a distal end that is configured to pass through the first lumen and through the first hole in the first wall section;
 extending the distal end of the first fluid-tight bag outside the ventricle so that at least a portion of the distal end of the first fluid-tight bag has a diameter that is larger than the first hole;
 introducing a first substance into the first fluid-tight bag in a fluid state via the first inlet after the distal end of the first fluid-tight bag has been extended, wherein the first substance is configured to solidify after being introduced into the first fluid-tight bag;
 passing a second catheter having a second lumen from inside the ventricle to outside the ventricle through a second hole in the second wall section;
 delivering, through the second catheter, a second fluid-tight bag having a second inlet that is configured to accept a fluid and a distal end that is configured to pass through the second lumen and through the second hole in the second wall section;

extending the distal end of the second fluid-tight bag outside the ventricle so that at least a portion of the distal end of the second fluid-tight bag has a diameter that is larger than the second hole;

introducing a second substance into the second fluid-tight bag in a fluid state via the second inlet after the distal end of the second fluid-tight bag has been extended, wherein the second substance is configured to solidify after being introduced into the second fluid-tight bag; and pulling the first substance towards the second substance after the first substance and the second substance have solidified.

16. The method of claim 15, wherein the step of introducing the first substance is implemented by pushing a first plunger through a first tube-shaped proximal portion of the first fluid-tight bag into the distal end of the first fluid-tight bag while the first substance is in a fluid state, and wherein the step of introducing the second substance is implemented by pushing a second plunger through a second tube-shaped proximal portion of the second fluid-tight bag into the distal end of the second fluid-tight bag while the second substance is in a fluid state.

17. The method of claim 16, further comprising the steps of:

withdrawing the first plunger via the first tube-shaped proximal portion after the first substance has solidified; and withdrawing the second plunger via the second tube-shaped proximal portion after the second substance has solidified.

18. The method of claim 15, wherein the step of extending the distal end of the first fluid-tight bag comprises extending the distal end of the first fluid-tight bag to a diameter of at least 2 cm, and wherein the step of extending the distal end of the second fluid-tight bag comprises extending the distal end of the second fluid-tight bag to a diameter of at least 2 cm.

19. The method of claim 15, wherein the step of extending the distal end of the first fluid-tight bag comprises extending the distal end of the first fluid-tight bag to a diameter between 3 and 6 cm, and wherein the step of extending the distal end of the second fluid-tight bag comprises extending the distal end of the second fluid-tight bag to a diameter between 3 and 6 cm.

* * * * *